(12) United States Patent
Ito et al.

(10) Patent No.: US 6,465,478 B1
(45) Date of Patent: Oct. 15, 2002

(54) 1,3,8-TRIUAZASPIRO(4,5)DECANONE COMPOUNDS AS ORL1-RECEPTOR AGONISTS

(75) Inventors: Fumitaka Ito, Aichi-ken (JP); Yoriko Ohashi, Aichi-ken (JP)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 09/426,824

(22) Filed: Oct. 22, 1999

Related U.S. Application Data

(63) Continuation of application No. PCT/IB98/01702, filed on Oct. 23, 1998.

(51) Int. Cl.$^7$ .................... A61K 31/438; C07D 471/10
(52) U.S. Cl. .......................... 514/278; 546/20
(58) Field of Search .................. 546/20; 514/278

(56) References Cited

U.S. PATENT DOCUMENTS 6,043,366 A * 3/2000 Adam et al. ............... 546/16

* cited by examiner

*Primary Examiner*—Charanjit S. Aulakh
(74) *Attorney, Agent, or Firm*—P. C. Richardson; P. H. Ginsburg; A. D. Joran

(57) ABSTRACT

A compound of formula:

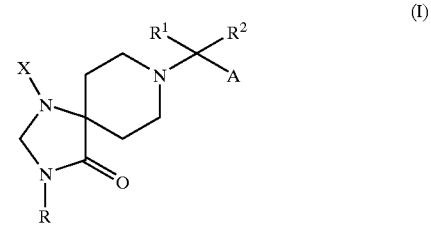

$R^1$ and $R^2$ are independently $C_1$–$C_4$ alkyl; or $R^1$ and $R^2$, taken together with the carbon atom to which they are attached, form a mono-, bi-, tri- or spiro-cyclic group having 3 to 13 carbon atoms, wherein the cyclic group is optionally substituted by one to five substituents; A is ($C_1$–$C_3$)alkyl, phenyl, benzyl or the like; R is hydrogen, ($C_1$–$C_3$)alkyl, amino-($C_1$–$C_6$)alkyl, heterocyclic-($C_1$–$C_3$)alkyl wherein the heterocyclic is optionally substituted by amino, (($C_1$–$C_4$)alkyl)-Z—($C_1$–$C_6$)alkyl wherein Z is OC(=O) or the like; and X is ($C_1$–$C_3$)alkyl, phenyl or the like. These compounds are useful as ORL1-receptor agonists, and useful as analgesics or the like in mammalian subjects.

7 Claims, No Drawings

1,3,8-TRIUAZASPIRO(4,5)DECANONE COMPOUNDS AS ORL1-RECEPTOR AGONISTS

This is a continuation of PCT/IB98/01702 filed Oct. 23, 1998.

TECHNICAL FIELD

This invention relates to 1,3,8-triazaspiro[4.5]decanone compounds or their pharmaceutically acceptable salts, pharmaceutical compositions containing them, and their medical uses. The compounds of this invention have activity as ORL1-receptor agonists, and are useful as an analgesic, anti-inflammatory, diuretic, anesthetic, neuroprotective, anti-hypertensive or anti-anxiety agent, or as an agent for appetite control or hearing regulation.

BACKGROUND ART

In spite of their usefulness as analgesics, usage of opioids such as morphine and heroin are strictly limited. This is because these drugs induce side effects such as euphoria or respiratory failure. Further, multiple dosage of the drugs cause addiction. Thus, there has been a long-felt need to provide less toxic analgesics.

Considerable pharmacological and biochemical studies have been carried out to identify opioid receptors and their endogenous ligands, and peptide and non-peptide opioid ligands have been discovered. In the recent past, amino acid sequences of mu- ($\mu$-), delta- ($\delta$-) and kappa ($\kappa$-)opioid receptor subtypes have been identified and reported. Subsequently, a novel receptor subtype was identified and termed ORL1-receptor, and Meunier, J.-C et al. reported the isolation and structure of the endogenous agonist of the receptor (*Nature*, Vol. 377, pp. 532–535, Oct. 12, 1995). It is suggested that the agonist for ORL1-receptor be effective in neurogenic inflammation (*Tips*, Vol. 18, pp. 293–300, August 1997). It is also suggested that the agonist be a potent analgesic having less psychological side effects and addiction (D. Julius, *Nature*, Vol. 377, p. 476, Oct. 12, 1995).

European Patent Publication No. EP 856514 A1 discloses a series of 8-substituted-1,3,8-triazaspiro[4.5]decan-4-one compounds as agonists and/or antagonists of the Orphanin EQ (OFQ) receptor.

BRIEF DISCLOSURE OF THE INVENTION

The present invention provides a compound of the following formula:

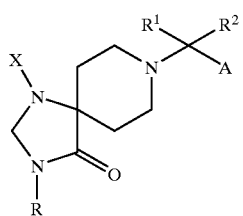

(I)

or its pharmaceutically acceptable salt, wherein
$R^1$ and $R^2$ are independently $C_1$–$C_4$ alkyl; or
$R^1$ and $R^2$, taken together with the carbon atom to which they are attached, form a mono-, bi-, tri- or spiro-cyclic group having 3 to 13 carbon atoms, wherein the cyclic group is optionally substituted by one to five substituents independently selected from halo, ($C_1$–$C_4$)alkyl, ($C_2$–$C_4$)alkenyl, ($C_1$–$C_4$)alkoxy, hydroxy, oxo, =$CH_2$ and =CH—($C_1$–$C_4$)alkyl, provided that the bi- or tri-cyclic group is not a benzo-fused ring;

A is ($C_1$–$C_7$)alkyl, ($C_2$–$C_5$)alkenyl, ($C_2$–$C_5$)alkynyl, phenyl-($C_1$–$C_5$)alkyl, phenyl or heteroaryl selected from furyl, thienyl, pyrrolyl and pyridyl, wherein the phenyl and heteroaryl are optionally substituted by one to three substituents selected from halo, ($C_1$–$C_3$)alkyl and ($C_1$–$C_3$)alkoxy;

R is hydrogen, ($C_1$–$C_6$)alkyl, ($C_2$–$C_6$)alkenyl, ($C_2$–$C_6$)alkynyl, ($C_3$–$C_7$)cycloalkyl, ($C_1$–$C_6$)alkanoyl, (($C_1$–$C_4$)alkyl)-Z—($C_1$–$C_6$)alkyl, (($C_3$–$C_7$)cycloalkyl)-Z—($C_1$–$C_6$)alkyl, heterocyclic-($C_1$–$C_6$)alkyl, phenyl-($C_1$–$C_6$)alkyl, heterocyclic-($C_1$–$C_6$)alkyl-Z—($C_1$–$C_6$)alkyl, phenyl-($C_1$–$C_6$)alkyl-Z—($C_1$–$C_6$)alkyl, heterocyclic-Z—($C_1$–$C_6$)alkyl, (($C_3$–$C_7$)cycloalkyl)-heterocyclic-($C_1$–$C_6$)alkyl, heterocyclic-heterocyclic-Z—($C_1$–$C_6$)alkyl, wherein the alkyl, alkenyl, alkynyl, cycloalkyl and heterocyclic are optionally substituted by one to three substituents selected from halo, hydroxy, amino, guanizino, carboxy, amidino, ureido, ($C_1$–$C_3$)alkyl, ($C_1$–$C_3$)alkoxy, and mono- or di-($C_1$–$C_4$)alkylamino, and wherein Z is O, S, SO, $SO_2$, CO, C(=O)O, OC(=O), N(R), C(=O)N(R) or N(R)CO (preferred R in Z is hydrogen or ($C_1$–$C_4$)alkyl); and X is phenyl, heterocyclic, ($C_1$–$C_6$)alkyl, ($C_2$–$C_6$)alkenyl, ($C_3$–$C_7$)cycloalkyl, ($C_2$–$C_7$)alkynyl, wherein the phenyl, heterocyclic, alkyl, alkenyl, cycloalkyl and alkynyl are optionally substituted by one to three substituents selected from halo, ($C_1$–$C_3$)alkyl and ($C_1$–$C_3$)alkoxy.

The term "alkyl", as used herein, unless otherwise indicated, includes saturated monovalent hydrocarbon radicals having straight, branched or cyclic moieties or combinations thereof.

The term "alkoxy", as used herein, includes O-alkyl groups wherein "alkyl" is defined above.

The term "halo", as used herein, refers to F, Cl, Br or I, preferably F or Cl.

The term "cycloalkyl", as used herein, means a saturated carbocyclic radical including, but not limited to, cyclopropyl, cyclobutyl, cyclopentyl, cyclohexyl, cycloheptyl, cyclooctyl, cyclononyl, cyclodecyl and the like.

The term "heterocyclic" means saturated, partially saturated or fully-unsaturated monocyclic or bicyclic hydrocarbon ring system which has one or more hetero atoms in the ring, preferably has 4 to 10 carbon atoms and 1 to 3 heteroatoms. Preferred heterocyclic includes, but not limited to, piperidino, piperidinyl, hexamethyleneimino, morpholino, thiamorpholino, pyrrolidino, pyrazolino, pyrazolidino, pyrazoryl, piperazinyl, furyl, thienyl, oxazolyl, tetrazolyl, thiazolyl, imidazolyl, imidazolinyl, pyrazolyl, pyridyl, pyrimidinyl, pyrrolyl, isoquinolyl, quinolyl, thiophenyl, pyrazinyl, pyridazinyl, aziridinyl and azetidinyl.

The term "mono-, bi- or tri-cyclic ring" means hydrocarbon cyclic groups of 3 to 13 carbon atoms, having one to three rings therein, and optionally having a double bond therein, including, but not limited to, cycloalkyl, cycloalkenyl, decahydronaphthalene, bicyclo[2.2.1.]heptane, bicyclo[3.2.1]octane, bicyclo[3.3.1]nonane, adamantane and tricyclo[5.2.1.0$^{2,6}$]decane.

The term "spirocyclic group" means a hydrocarbon spirocyclic group of 6 to 13 carbon atoms, including, but not limited to, spiro[5.5]undecanyl and spiro[4.5]decanyl.

The term "treating", as used herein, refers to reversing, alleviating, inhibiting the progress of, or preventing the disorder or condition to which such term applies, or one or more symptoms of such disorder or condition. The term "treatment" as used herein refers to the act of treating, as "treating" is defined immediately above.

A preferred group of the compounds of the present invention includes the compounds of Formula (I), wherein $R^1$ and $R^2$ are independently $(C_1-C_4)$alkyl; or $R^1$ and $R^2$, taken together with the carbon atom to which they are attached, form a monocyclic group selected from $(C_3-C_{13})$cycloalkyl and $(C_3-C_{13})$cycloalkenyl, wherein the monocyclic group is optionally substituted by one or two substituents independently selected from halo and $(C_1-C_4)$alkyl;

A is phenyl-$(C_1-C_5)$alkyl or phenyl optionally substituted by one to three substituents independently selected from halo, $(C_1-C_3)$alkyl and $(C_1-C_3)$alkoxy;

R is hydrogen, $(C_1-C_6)$alkyl, $(C_2-C_6)$alkenyl, heterocyclic-$(C_1-C_6)$alkyl or $((C_1-C_4)$alkyl)-Z—$(C_1-C_6)$alkyl, wherein the alkyl, alkenyl and heterocyclic are optionally substituted by one to three substituents selected from halo, hydroxy, amino, guanizino, carboxy, amidino, ureido, $(C_1-C_3)$alkyl, $(C_1-C_3)$alkoxy, mono- and di-$(C_1-C_4)$alkylamino; and X is phenyl, heterocyclic, $(C_1-C_6)$alkyl or $(C_2-C_6)$alkenyl, wherein the phenyl, heterocyclic, alkyl and alkenyl are optionally substituted by one to three substituents selected from halo, $(C_1-C_3)$alkyl and $(C_1-C_3)$alkoxy.

A more preferred group of this invention includes the compounds of Formula (I), wherein $R^1$ and $R^2$, taken together with the carbon atom to which they are attached, form a monocyclic group selected from $(C_5-C_{10})$cycloalkyl and $(C_5-C_{10})$cycloalkenyl, wherein the monocyclic group is optionally substituted by one or two substituents independently selected from $(C_1-C_3)$alkyl; A is phenyl or benzyl; R is hydrogen, $(C_1-C_3)$alkyl, amino-$(C_1-C_6)$alkyl, heterocyclic-$(C_1-C_3)$alkyl wherein the heterocyclic is optionally substituted by amino or $((C_1-C_4)$alkyl)-Z—$(C_1-C_6)$alkyl wherein Z is OC(=O); and X is $(C_1-C_3)$alkyl or phenyl.

A further preferred group of this invention includes the compounds of Formula (I), wherein $R^1$ and $R^2$, taken together with the carbon atom to which they are attached, form cyclohexyl, cycloheptyl or cycloheptenyl; A is phenyl or benzyl (more preferably phenyl); R is hydrogen, aminopropyl, aminohexyl, piperidinylethyl, 4-aminopiperidinylethyl or methoxy-carbonylmethyl; and X is phenyl.

Particularly preferred individual compounds are:

3-(3-aminopropyl)-1-phenyl-8-(1-phenylcycloheptyl)-1,3, 8-triazaspiro[4.5]decan-4-one;

8-(1-methylcycloheptyl)-1-phenyl-1,3,8-triazaspiro[4.5] decan-4-one; and its pharmaceutically acceptable salts.

This invention also relates to a pharmaceutical composition for the treatment of a disorder or condition mediated by ORL1-receptor and its endogenous ligands in a mammal including a human, or for anesthetizing a mammal including a human, which comprises an effective amount of the compound of Formula 1, or a pharmaceutically acceptable salt thereof, and a pharmaceutically acceptable carrier.

More specifically, this invention relates to a pharmaceutical composition for the treatment of a disorder or condition selected from the group consisting of inflammatory diseases, inflammation-related hyperalgesia, eating disorders, arterial blood pressure disorders, tolerance to narcotic analgesics, dependence on narcotic analgesics, anxiety, stress disorders, psychic trauma, schizophrenia, Parkinson's disease, chorea, depressant, Alzheimer's disease, dementias, epilepsy and convulsions, useful as analgesics, anesthetics, neuroprotective agents or analgesic enhancers, or useful for controlling water balance, hearing regulation, controlling sodium ion excretion or ameliorating brain function, comprising an amount of a compound of Formula 1, or a pharmaceutically acceptable salt thereof that is effective in treating such disorder or condition in a mammal including a human, and a pharmaceutically acceptable carrier.

This invention relates to a method of treating a disorder or condition, or anesthetizing a mammal including a human, the treatment and anesthetization of which can be effected or facilitated by activating ORL1-receptor in a mammal including a human, comprising administering to a mammal in need of such treatment an effective amount of a compound of Formula 1 or a pharmaceutically acceptable salt thereof.

More specifically, this invention relates to a method for treating a disorder or condition in a mammal including a human, where the disorder or condition is selected from the group consisting of inflammatory diseases, inflammation-related hyperalgesia, eating disorder, arterial blood pressure disorders, tolerance to narcotic analgesics, dependence on narcotic analgesics, anxiety, stress disorders, psychic trauma, schizophrenia, Parkinson's disease, chorea, depressant, Alzheimer's disease, dementias, epilepsy and convulsions, or for anesthetizing a mammal including a human, or for alleviating pain, producing a neuroprotective effect, enhancing analgesic, controlling water balance, hearing regulation, controlling sodium ion excretion or ameliorating brain function in a mammal including a human, comprising administering to said mammal an effective amount of a compound of Formula 1 or a pharmaceutically acceptable salt thereof and a pharmaceutically acceptable carrier.

DETAILED DISCLOSURE OF THE INVENTION

The following reaction Schemes illustrate the preparation of the compounds of the present invention. Unless otherwise indicated, $R^1$, $R^2$, A, R and X in the reaction Schemes and discussion that follow are defined above.

In the preparation processes hereafter described, amino or carbonyl groups may be protected according to known procedures such as those disclosed in Protective Group in Organic Synthesis by T. W. Greene et al. (John Wiely & Sons, 1991). Typical amino protecting groups include benzyl, ethoxycarbonyl, and t-butoxycarbonyl (abbreviated as t-Boc or Boc). Carbonyl groups may typically be protected as acetals, thioacetals, hydrazaones, oximes and cyanohydrines, which can readily removed treatment in the presence of an acid or Lewis acid.

General Synthesis

The ORL1 agonists of Formula (I) of this invention may be prepared according to the following methods.

Reaction Scheme 1 illustrates a method for the preparation of Compound (I).

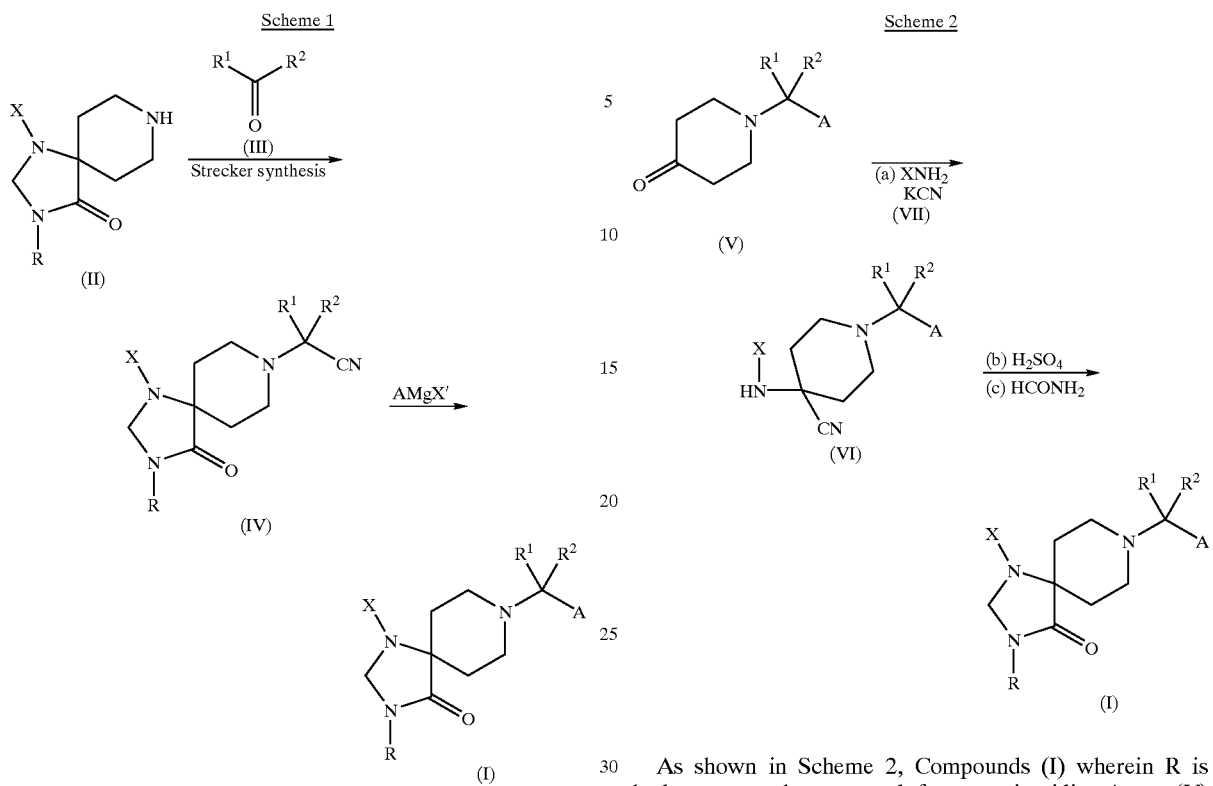

As shown in Scheme 1, Compounds (I) may be obtained from a 1,3,8-triazaspiro[4.5]decanone (II) via intermediate (IV). First, Compound (II) may be subjected to the Strecker synthesis with the stoichiometric amount of ketone (III). Second, Compound (IV) can be subjected to Grignard reaction with a reagent represented by the formula AMgX' (X' is for example halo) to give Compounds (I).

The Strecker synthesis can be carried out using a suitable cyanating agent according to known procedures reported by A. Kalir, et al., (*J. Med. Chem.* 1969, 12, 473). Suitable cyanating agents include cyanide such as potassium cyanide (KCN). This reaction can be carried out at pH of about 3 to 11, at a temperature of 0° to 50° C., preferably in ice-cool water for 30 min. to 7 days. The Grignard reaction can be carried out under unhydrous condition according to known procedures (e.g., O. A. Al-Deeb, *Arzneim.-Forsch./Drug Res.*, 1994, 44, 1141). More specifically, this reaction can be carried out in a suitable solvent such as tetrahydrofuran (THF), at from about room temperature (e.g., 20° C.) to the reflux temperature of the solvent for 30 minutes to 48 hours.

Compounds (I) wherein $R^1$ and $R^2$, taken together with the carbon atom to which they are attached, form a monocyclic, bicyclic, tricyclic or spirocyclic ring can be also prepared by subjecting an intermediate (II) to the Grignard reaction according to the similar procedures illustrated in Scheme 1. The suitable Grignard reagents are those represented by the formula of $R^1R^2ACMgX'$ wherein $R^1$ and $R^2$, taken together with the carbon atom to which they are attached, form the cyclic ring; and X' is halo.

Compounds (I) can be also prepared by the methods illustrated in Scheme 2.

As shown in Scheme 2, Compounds (I) wherein R is hydrogen can be prepared from a piperidine-4-one (V) through a compound (VI) according to known procedures as described in U.S. Pat. No. 3,238,216. First, the compound (V) can be reacted with a hydrochloric acid salt of an amino compound (VII) (i.e., $XNH_2$) in the presence of a suitable cyanating agent such as potassium cyanide (KCN), to give the compound (VI). This reaction can be carried out in a suitable reaction inert solvent such as water at 0° to 50° C. for 30 min. to 7 days. Then, the compound (VI) may be treated with sulfuric acid at 0° to 100° C. for 30 min. to 10 hours, followed by reaction with formamide ($HCONH_2$). The reaction with formamide may be carried out at 150° to 250° C. for 30 min. to 20 hours. If a mixture of 1-phenyl-1,3,8-triazaspiro[4.5]decan-4-one derivative and 1-phenyl-1,3,8-triazaspiro[4.5]dec-2-en-4-one derivative is obtained in this reaction condition, the mixture may be treated with a reducing reagent such as sodium borohydride ($NaBH_4$) to give desired 1-phenyl-1,3,8-triazaspiro[4.5]decan-4-one derivative.

A compound of Formula (I) wherein R is hydrogen obtained as above can be subjected to suitable reactions for replacing R with other substituents. For example, the compound of formula (I) wherein R is hydrogen can be subjected to nucleophilic substitution reactions. It should be understood by a skilled person in the art that the nucleophilic substitution reactions can conveniently be conducted in the presence of a base. If desired, a phase transfer catalyst such as tetrabutylammonium hydrogen sulfate ($Bu_4NHSO_4$) can be used in the reactions.

For example, a compound of Formula (I) wherein R is alkyl, substituted alkyl or the like can be prepared by reacting a compound of Formula (I) wherein R is hydrogen with a suitable nucleophile. Suitable leaving groups in the nucleophiles include sulfonate such as mesylate and tosylate, and halo. Suitable bases used in the reactions include sodium hydride (NaH), sodium hydroxide and the like. The reactions can be carried out in a reaction inert solvent such as DMF and THF at a temperature from about 0° to 100° C. for from about 0.5 to 24 hours.

In the above reactions, amino or hydroxy groups can be protected, then the protecting groups can be removed after the reactions according to procedures known by those skilled in the art. Removal of amino protecting group can conveniently be carried out by treating the resultant amino-protected compound with an acid such as hydrochloride. Removal of hydroxy protecting group can conveniently be carried out by treating the resultant hydroxy protected compound with a reducing agent such as LiAlH$_4$.

Compounds of Formula (I) thus obtained wherein R is hydroxy alkyl can be modified by inverting the hydroxy group into other substituent. This modification can be carried out in reactions comprising introduction of a functional group and subsequent nucleophilic substitution reaction. Suitable functional groups include sulfonate such as tosylate and mesylate, and halo. The introduction of functional group can be carried out in the absence or presence of a base such as triethylamine in a reaction inert solvent such as ethanol, DMSO, cyclohexane, dichloromethane or the like. The nucleophilic substitution reaction can typically be carried out using an amine compound as a nucleophile. This reaction can be carried out in the presence of a base such as potassium carbonate or the like, in a reaction inert solvent such as DMF or the like, at a temperature from about 0° to 100° C., and for from about 0.5 to 24 hours.

Intermediates (V) can be prepared by the methods illustrated in Scheme 3.

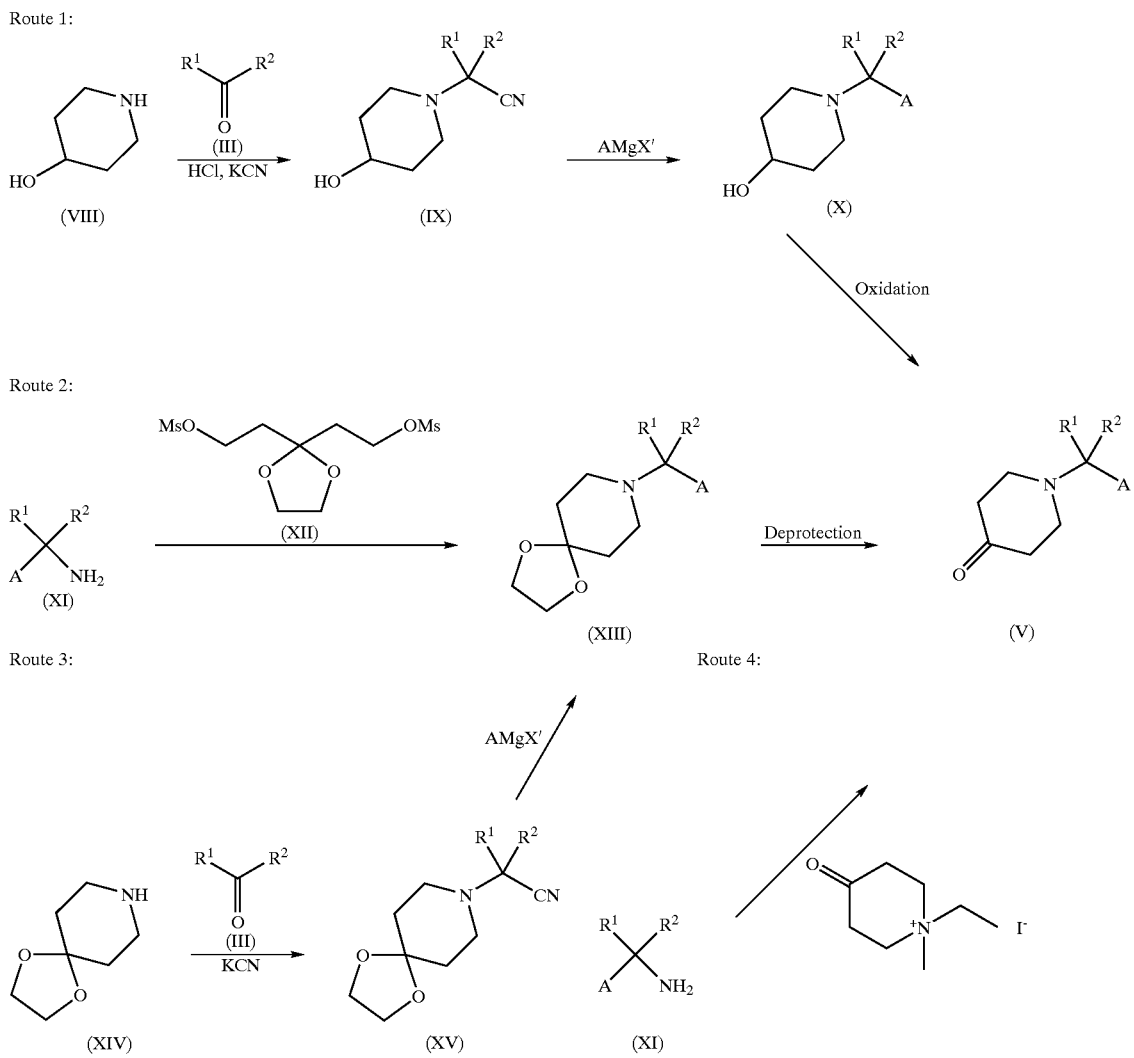

Scheme 3

Route 1 illustrates a preparation of Compound (V) from known 4-piperidinol (VIII) according to the procedures reported by A. Kalir et al., *J. Med. Chem.*, 1969, 12, 473. First, Compound (VIII) can be condensed with Compound (III) and cyanated to give Compound (IX). Second, obtained Compound (IX) can be subjected to the Grignard reaction with AMgX' wherein X' is halo to give Compound (X). Then, Compound (X) can be oxidized to give Compound (V).

Route 2 illustrates a preparation of Compound (V) from a starting amine (XI) 10 comprising condensation of (XI) with 3,3-ethylenedioxypentane-1,5-diol dimethanesulfonate (XII) followed by deprotection. These reactions can be carried out under known conditions (e.g., B. de Costa et al., *J. Chem. Soc., Perkin Trans.* I, 1992, 1671).

Route 3 illustrates a preparation of Compound (V) from a known 4-piperidone ethylene ketal (XIV). This preparation comprises (a) condensation of (XIV) with (III), (b) cyanation, (c) the Grignard reaction and (d) deprotection. These reactions can be carried out under the same conditions described in Scheme 1.

As shown in Route 4, Compound (V) can be prepared directly from a starting amine (XI) using N-ethyl-N-methyl-4-oxopiperidinium iodide according to the procedure of D. M. Tschaen et al (*J. Org. Chem.* 1995, 60, 4324).

The starting amines (XI) can be readily prepared by known methods for a skilled person (e.g., J. Weinstock, et al., OS IV 910, E. J. Cone, et al., *J Med. Chem.*, 1981, 24, 1429, and Ritter Reaction described in *Org. React.*, 1969, 17, 313).

Unless indicated otherwise, the present pressure of each of the above reactions is not critical. Generally, the reactions will be conducted at a pressure of about one to about three atmosphere, preferably at ambient pressure (about one atmosphere).

The compounds of Formula (I) of this invention are basic, therefore they will form acid-addition salts. All such salts are within the scope of this invention. However, it is necessary to use an acid addition salts which is pharmaceutically-acceptable for administration to a mammal. The acid-addition salts can be prepared by standard methods. For example, the salts may be prepared by contacting the basic compounds with acid in substantially equivalent proportions in water or an organic solvent such as methanol or ethanol, or a mixture thereof. The salts can be isolated by crystallization from or evaporation of the solvent. Typical salts which can be formed are the hydrochloride, nitrate, sulfate, bisulfate, phosphate, acetate, lactate, citrate, tartrate, succinate, maleate, fumarate, gluconate, saccharate, benzoate, methanesulfonate, p-toluenesulfonate, oxalate and pamoate (1,1'-methylene-bis-(2-hydroxy-3-naphtoate)) salts.

The compounds of Formula (I) have been found to possess selective affinity for ORL1-receptors and ORL-1 receptor agonist activity. Thus, these compounds are useful as an analgesic, anti-inflammatory diuretic, anesthetic, neuroprotective, anti-hypertensive or an anti-anxiety agent, or an agent for appetite control or hearing regulation, in mammalian subjects, especially humans in need of such agents. These compounds are also useful as agents for the treatment of the other psychiatric, neurological and physiological disorders such as depression, trauma, memory loss due to Alzheimer's disease or other dementias, epilepsy and convulsions, symptoms of withdrawal from drugs of addiction, control of water balance, sodium excretion, and arterial blood pressure disorders. These compounds are particularly useful as an analgesic, anti-inflammatory diuretic or anesthetic.

The subject invention also includes isotopically-labelled compounds, which are identical to those recited in formula (I), but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorus, fluorine and chlorine, such as $^2$H, $^3$H, $^{13}$C, $^{14}$C, $^{15}$N, $^{18}$O, $^{17}$O, $^{31}$P, $^{32}$P, 35S, $^{18}$F, and $^{36}$Cl, respectively. Compounds of the present invention, prodrugs thereof, and pharmaceutically acceptable salts of said compounds or of said prodrugs which contain the aforementioned isotopes and/or other isotopes of other atoms are within the scope of this invention. Certain isotopically-labelled compounds of the present invention, for example those into which radioactive isotopes such as $^3$H and $^{14}$C are incorporated, are useful in drug and/or substrate tissue distribution assay. Tritiated, i.e., $^3$H, and carbon-14, i.e., $^{14}$C, isotopes are particularly preferred for their ease of presentation and detectability. Further, substitution with heavier isotopes such as deutrium, i.e., $^2$H, can afford therapeutic advantage resulting from greater metabolic stability, for example increased in vivo half-life or reduced dosage requirement and, hence, may be preferred in some circumstances. Isotopically labelled compounds of formula (I) of this invention and prodrugs thereof can generally be prepared by carrying out the procedure disclosed in above-disclosed Schemes and/or Examples and Preparations below, by submitting a readily available isotopically labelled reagent for a non-isotopically labelld reagent.

The affinity, agonist activities and analgesic activity can be demonstrated by the following tests respectively.

Selective Affinity for ORL1-receptors

ORL1-receptor Affinity

The ORL1 receptor binding affinity of the compounds of this invention are determined by the following procedures. Human ORL1 receptor transfected HEK- 293 cell membranes and wheat-germ agglutinin coated SPA beads are combined with 0.4 nM[3H]nociceptin and unlabeled test compounds in 200 µl of 50 mM Hepes buffer pH7.4 containing 10 MM MgCl$_2$ and 1 mM EDTA. This mixture is incubated at room temperature (abbreviated as rt) for 30 min to 60 min. Non specific binding is determined by the addition of 1 µM nociceptin. Radioactivity is counted by Wallac 1450 MicroBeta.

µ-receptor Affinity

The mu (µ) opioid receptor binding affinity of the compounds of this invention are determined by the following procedures. Human-mu opioid receptor transfected CHO-K1 cell membranes and wheat-germ agglutinin coated SPA beads are combined with 1.0 nM[3H]DAMGO and unlabeled test compounds in 200 µl of 50 mM Hepes buffer pH7.4 containing 10 mM MgCl$_2$ and 1 mM EDTA. This mixture is incubated at rt for 30 min to 60 min. Non specific binding is determined by the addition of 1 µM DAMGO. Radioactivity was counted by Wallac 1450 MicroBeta.

κ-receptor Affinity

The kappa (κ) opioid receptor binding affinity of the compounds of this invention are determined by the following procedures. Human kappa-opioid receptor transfected CHO-K1 cell membranes and wheat-germ agglutinin coated SPA beads are combined with 0.5 nM[3H]CI-977 and unlabeled test compounds in 200 µl of 50 mM Hepes buffer pH7.4 containing 10 mM MgCl$_2$ and 1 mM EDTA. This mixture is incubated at rt for 30 min to 60 min. Non specific binding is determined by the addition of 1 µM CI-977. Radio activity is counted by Wallac 1450 MicroBeta.

δ-receptor Affinity

The delta (δ) opioid receptor binding affinity of the compounds of this invention are determined by the following procedures. Human delta opioid receptor transfected CHO-K1 cell membranes and wheat-germ agglutinin coated SPA beads are combined with 2.0 nM[3H]DPDPE and unlabeled test compounds in 200 µl of 50 mM Hepes buffer pH7.4 containing 10 mM MgCl$_2$ and 1 mM EDTA. The assay is incubated at room temperature for 30 min to 60 min. Non specific binding are determined by the addition of 1 µM of each non-labeled ligands. Radioactivity is counted by Wallac 1450 MicroBeta.

Each percent non specific binding thus obtained is graphed as a function of compound concentration. A sigmoidal curve is used to determine IC$_{50}$ values.

All compounds of Example 1 through 8 were tested by the above procedures and demonstrated good affinity for ORL1-receptors. In this testing, the above-mentioned particularly preferred compounds demonstrated higher affinity for ORL1-receptors than for mu-receptors (i.e., $IC_{50}$ for ORL1-receptors/$IC_{50}$ for mu-receptors were less than 1.0).

Functional Assay

The functional activity of the compounds of this invention in each opioid receptor can be determined in 35S-GTPγS binding system according to the procedures reported by L. J. Sim, R. Xiao and S. Childers *Neuroreort* Vol. 7, pp. 729–733, 1996. Each human ORL1-, mu-, kappa- and delta-receptor transfected CHO-K1 or HEK cell membranes are used. The membranes are suspended in ice-cold 20 mM HEPES buffer pH 7.4, containing 100 mM NaCl, 10 mM $MgCl_2$ and 1 mM EDTA. 0.17 mg/ml of Dithiothreitol (DTT) is added to this buffer prior to use. Membranes are incubated at 25° C. for 30 minutes with the appropriate concentration of test compounds in the presence of 5 μM GDP, 0.4 nM of 35S-GTPγS and Wheat-germ agglutinin (WGA) coated SPA bead (1.5 mg) in a 0.2 ml total volume. Basal binding is assessed in the absence of agonist, and non-specific binding is determined with 10 μM GTPγS. Radio activity is counted by Wallac 1450 MicroBeta.

Analgesic Tests

Tail Flick Test

Male ICR mice, 4 weeks old and weighing 19–25 g, are used. The training sessions are performed until mice can flick their tails within 4.0 sec by using Analgesia Meter MK-330A (Muromachi Kikai, Japan). Selected mice are used in this experiment. The latency time is recorded twice at 0.5, 1.0, and 2.0 h after administration of the compound. The intensity of the beam is set to 80. Cut-off time is set to 8.0 sec. A compound of this invention is subcutaneously administered 30 min before the test. The $ED_{50}$ value, defined as the dose of the compounds tested which halves the tail flicking is observed in the control group.

Acetic Acid Writhing Test

Male ICR mice, 4 weeks old and weighing 21–26 g, are used. They are fasted the day before use. Acetic acid is diluted with saline to the concentration of 0.7%(v/v) and injected intraperitoneally (0.2 ml/10 g of body weight) to mice with a 26 gauge needle. A compound of this invention is dissolved in 0.1% methyl cellulose(MC)-saline and subcutaneously administered to mice 0.5 h before acetic acid injection. After the acetic acid injection, each animal is placed in a 1 L beaker and recorded by a video tape recorder. Number of writhing is counted from 5 to 15 min after acetic acid injection. The $ED_{50}$ value, defined as the dose of the compounds tested which halves the writhing is observed in the control group. Some compounds of this invention demonstrated good analgesic activity in this test (i.e., $ED_{50}$ value of 0.02 mg/kg to 1 mg/kg).

Formalin Licking Test

Male SD rats (80–100 g) are injected subcutaneously with a test compound dissolved in 0.1% methyl cellulose(MC)-saline or vehicle. After 30 min, 50 μl of a 2% formalin are injected into a hind paw. The number of licking the injected paw per observation period is measured from 15 to 30 min. after the injection of formalin and expressed as % inhibition compared to the respective vehicle group. This testing method is described in, for example, (1) R. L. Follenfant, et.al., Br. J. Pharmacol. 93, 85–92 (1988); (2) H. Rogers, et.al., Br. J. Pharmacol. 106, 783–789 (1992); and (3) H. Wheeler-Aceto, et al., Psychopharmacology, 104, 35–44 (1991).

The compounds of Formula (I) of this invention can be administered by conventional pharmaceutical practice via either the oral, parenteral or topical routes to mammals, for the treatment of the indicated diseases. For administration to human patient by either route, the dosage is in the range of about 0.01 mg/kg to about 3000 mg/kg body weight of the patient per day, preferably about 0.01 mg/kg to about 1000 mg/kg body weight per day, more preferably about 0.1 mg/kg to about 100 mg/kg body weight per day administered singly or as a divided dose. However, variations will necessarily occur depending upon the weight and condition of the subject being treated, compound employed, the disease state being treated and the particular route of administration chosen.

The compounds of the present invention may be administered alone or in combination with pharmaceutically acceptable carriers by either of the above routes previously indicated, and such administration can be carried out in single or multiple doses. Generally, the compounds can be combined with various pharmaceutically acceptable carriers in the form of tablets, powders, capsules, lozenges, trochees, hard candies, powders, sprays, creams, salves, suppositories, jellies, gels, pastes, lotions, ointments, suspensions, solutions, elixirs, syrups or the like. Such pharmaceutical carriers include solvents, excipients, coating agents, bases, binders, lubricants, disintegrants, solubilizing agents, suspending agents, emulsifing agents, stabilizers, buffering agents, tonicity agents, preservatives, flavorating agents, aromatics, coloring agents and the like.

For example, the tablets can contain various excipients such as starch, lactose, glucose, microcrystalline cellulose, calcium sulfate, calcium carbonate, talc, titanium oxide and the like, coating agents such as gelatin, hydroxypropylcellulose and the like, binding agents such as gelatin, gum arabic, methylcellulose and the like, and the disintegrating agents such as starch, agar, gelatine, sodium hydrogencarbonate and the like. Additionally, lubricating agents such as magnesium stearate and talc are often very useful for tabletting purposes. Solid compositions of a similar type may also be employed as fillers in gelatine capsules; preferred materials in this connection also include lactose as well as high molecular weight polyethylene glycols. When aqueous suspensions and/or elixirs are desired for oral administration, the active ingredient may be combined with various sweetening or flavoring agents, coloring matter or dyes, and, if so desired, emulsifying and/or suspending agents as well, together with diluents such as water, ethanol, propylene glycol, glycerin and various like combinations thereof.

In general, the therapeutically-effective compounds of this invention are present in such oral dosage forms at concentration levels ranging 5% to 70% by weight, preferably 10% to 50% by weight.

The compounds of the present invention in the form of a solution may be injected parenterlly such as intradermaly, subcutaneously, intravenously or intramuscularly. For example the solutions are sterile aqueous solutions, aqueous suspensions and an edible oil solutions. The aqueous solutions may be suitably buffered (preferably pH>8), and may contain enough salts or glucose to make the solution isotonic with blood. The aqueous solutions are suitable for intravenous injection purposes. The aqueous suspensions may contain a suitable dispersing or suspending agents such as sodium carboxymethylcellulose, methylcellulose, polyvinylpyrrolidone or gelatin. The aqueous suspensions can be used for subcutaneous or intramuscular injections. The edible oil such as cottonseed oil, sesame oil, coconut oil or peanut oil can be employed for the edible oil solutions. The oil solutions are suitable for intra-articular, intramuscular and subcutaneous injection. The preparation of all these solutions under sterile conditions is readily accomplished by standard pharmaceutical techniques well-known to those skilled in the art.

It is also possible to administer the compounds of the present invention topically when treating inflammatory conditions of the skin and this may preferably be done by way of creams, jellies, gels, pastes, ointments and the like, in accordance with standard pharmaceutical practice.

EXAMPLES AND PREPARATION

The present invention is illustrated by the following examples and preparation. However, it should be understood that the invention is not limited to the specific details of these examples and preparations. Melting points were taken with a Buchi micro melting point apparatus and is not corrected. Infrared Ray absorption spectra (IR) were measured by a Shimadzu infrared spectrometer (IR-470). $^1$H and $^{13}$C nuclear magnetic resonance spectra (NMR) were measured in CDCl$_3$ by a JEOL NMR spectrometer (JNM-GX270, 270 MHz) unless otherwise indicated and peak positions are expressed in parts per million (ppm) downfield from tetramethylsilane. The peak shapes are denoted as follows: s, singlet; d, doublet; t, triplet; m, multiplet; br, broad.

Preparation 1

1-(4-Oxo-1-phenyl-1,3,8-triazaspiro[4.5]dec-8-yl) cycloheptane-carbonitrile

To a stirred mixture of 1-(4-oxo-1-phenyl-1,3,8-triazaspiro[4.5]decane hydrochloride (578.8 mg, 2.16 mmol) and cycloheptanone (304 μl, 2.59 mmol) was added a solution of KCN (169 mg, 2.59 mmol) in water (1 ml) at room temperature. The reaction mixture was vigorously stirred at room temperature for 20 h. The precipitated white solid was collected by filtration, washed with water and hexane, and dried under vacuum at 50° C. for 1 h to afford 323 mg (42.4 %) of white powder.

$^1$H NMR (270 MHz, CDCl$_3$) δ7.58 (1H, br.s), 7.32–7.26 (2H, m), 6.93–6.84 (3H, m), 4.76 (2H, s), 3.00–2.96 (4H, m), 2.72–2.61 (2H, m), 2.20–2.15 (2H, m), 2.01–1.67 (12H, m)

Example 1

1-Phenyl-8-(1-phenylcycloheptyl)-1,3,8-triazaspiro[4.5]decan-4-one

To a stirred solution of 1-(4-oxo-1-phenyl-1,3,8-triazaspiro[4.5]dec-8-yl)cycloheptane-carbonitrile (323 mg, 0.916 mmol) in THF (6 ml) was added phenylmagnesium bromide (3M solution in diethyl ether, 3.05 ml, 9.16 mmol) at room temperature. Then the reaction mixture was stirred at room temperature for 24 h. The reaction mixture was poured into ice water, then extracted with CH$_2$Cl$_2$. The extracts combined were dried (Na$_2$SO$_4$), filtered, and concentrated. The residue was purified by preparative TLC (CH$_2$Cl$_2$/MeOH:10/1 to give 70.5 mg (19.1%) of title compound.

MS m/z(EI direct): 403(M$^+$), 375, 347, 325, 228, 172, 117.

$^1$H NMR (270 MHz, CDCl$_3$) δ7.60–7.50 (2H, m), 7.40–7.15 (5H, m), 7.05–6.80 (4H, m), 4.70 (2H, s), 2.95–2.70 (4H, m), 2.65–2.47 (2H, m), 2.20–2.00 (4H, m), 1.90–1.40 (10H, m).

This free amine was converted to HCl salt by treating with HCl solution in methanol. After evaporation of the solvent, the resulting white amorphous solid was collected by filtration to afford amorphous solid.

IR(KBr):3400, 1709 cm$^{-1}$

Anal. Calcd for C$_{26}$H$_{33}$N$_3$O.HCl.1H$_2$O: C, 68.18; H, 7.92; N, 9.17. Found: C, 68.29; H, 7.76; N, 9.23.

Example 2

3-(3-Aminopropyl)-1-phenyl-8-(1-phenylcycloheptyl)-1,3,8-triazaspiro[4.5]decan-4-one This was prepared according to the procedure of A. Petric et al. (*Bioorg. Med. Chem. Lett.* 1998, 8, 1455). To a stirred solution of 1-phenyl-8-(1-phenylcycloheptyl)-1,3,8-triazaspiro[4.5]decan-4-one (54.3 mg, 0.135 mmol) in toluene (0.3 ml) was added a solution of NaOH (23.8 mg, 0.595 mmol) in water (0.5 ml), n-Bu$_4$NHSO$_4$ (70.8 mg, 0.209 mmol), and a solution of N-(t-butoxycarbonyl)-3-bromopropylamine (65.3 mg, 0.274 mmol, this was reported by B. H. Lee et al. *J. Org. Chem.* 1983, 48, 24) in toluene (0.7 ml) at room temperature. The reaction mixture was stirred at room temperature for 18 h, then at 90° C. for 2 h. The reaction mixture was cooled down to room temperature, diluted with water, and extracted with CH$_2$Cl$_2$. The extracts combined were washed with brine, dried (Na$_2$SO$_4$), filtered, and concentrated. The residue was purified by preparative TLC (1 mm plate×2, CH$_2$Cl$_2$/MeOH:95/5, two times developed) to afford 54.2 mg (71.8%) of colorless solid.

$^1$H NMR (270 MHz, CDCl$_3$) δ7.55–7.52 (2H, m), 7.33–7.15 (5H, m), 6.94–6.82 (3H m), 5.22 (1H, br.s), 4.64 (2H, s), 3.49–3.43 (2H, m), 3.17–3.08 (2H, m), 2.93–2.84 (2H, m), 2.76–2.49 (2H, m), 2.18–2.01 (4H, m), 1.78–1.51 (14H, m), 1.43 (9H, s).

A solution of this Boc derivative (54.2 mg) in HCl solution in MeOH (2 ml) was stirred at room temperature for 15 h. Evaporation of the solvent gave solid which was dried under vacuum at 45° C. to give 35 mg of solid, mp 150–154° C. as HCl salt.

$^1$H NMR (270 MHz, DMSOd$_6$) δ10.45–10.30 (1H, m), 7.90 (3H, br.s), 7.72–7.69 (2H, m), 7.45–7.30 (4H, m), 7.20–7.05 (4H, m), 6.75–6.63 (1H, m), 4.57 (2H, s), 3.55–3.13 (8H, m), 3.05–2.85 (2H, m), 2.80–2.55 (4H, m), 2.45–2.30 (1H, m), 1.85–1.00 (10H, m).

IR(KBr): 3400, 1686 cm$^{-1}$

MS(ESI positive) m/z: 461(M+H)$^+$.

Anal. Calcd for C$_{29}$H$_{40}$N$_4$O.2HCl.2.5H$_2$O: C, 60.20; H, 8.19; N, 9.68. Found: C, 60.45; H, 8.22; N, 9.47.

Example 3

1-Phenyl-8-(1-phenylcycloheptyl)-3-[2-(1-piperidinyl)ethyl]-1,3,8-triazaspiro[4.5]decan-4-one This was prepared according to the procedure described in Example 2 using 1-(2-chloroethyl)piperidine hydrochloride instead of N-(t-butoxycarbonyl)-3-bromopropylamine, and 90° C. for 23 h instead of room temperature for 18 h then at 90° C. for 2 h to give HCl salt, mp 174–178° C. Yield was 31%.

IR(KBr): 3400, 1693 cm$^{-1}$

MS m/z(EI direct): 514(M$^+$), 457, 341, 325, 286, 237, 172, 98.

Anal. Calcd for C$_{33}$H$_{46}$N$_4$O.2HCl.3H$_2$O: C, 61.77; H, 8.48; N, 8.73. Found: C, 61.74; H, 8.72; N, 8.49.

A part of this hydrochloride salt was converted to free amine.

¹H NMR (270 MHz, CDCl₃) δ7.60–7.48 (2H, m), 7.40–7.15 (5H, m), 7.00–6.80 (3H, m), 4.70 (2H, s), 3.51 (2H, t, J=6.5 Hz), 3.00–2.30 (12H, m), 2.20–1.95 (4H, m), 1.90–1.35 (16H, m).

Example 4

8-(1-Methylcycloheptyl)-1-phenyl-1,3,8-triazaspiro[4.5]decan-4-one

This was prepared according to the procedure described in Example 1 using methylmagnesium bromide instead of phenylmagnesium bromide. Yield was 30%.

¹H NMR (270 MHz, DMSOd₆) δ10.11–9.96 (1H, m), 9.02 (1H, s), 7.26–7.11 (5H, m), 6.83–6.76 (1H, m), 4.62 (2H, s), 3.86–3.66 (2H, m), 3.11–2.92 (2H, m), 2.16–2.06 (2H, m), 1.91–1.46 (14H, m), 1.45 (3H, s).

IR(KBr): 1711 cm⁻¹

MS(ESI positive) m/z: 342(M+H)⁺.

Anal. Calcd for $C_{21}H_{31}N_3O \cdot 2HCl \cdot 0.3H_2O$: C, 60.08; H, 8.07; N, 10.01. Found: C, 60.26; H, 8.26; N, 10.00.

Example 5

8-(1-Methylcycloheptyl)-1-phenyl-3-[2-(1-piperidinyl)ethyl]-1,3,8-triazaspiro[4.5]decan-4-one This was prepared according to the procedure described in Example 3 using 8-(1-methylcycloheptyl)-1-phenyl-1,3,8-triazaspiro[4.5]decan-4-one instead of 1-phenyl-8-(1-phenylcycloheptyl)-1,3,8-triazaspiro[4.5]decan-4-one to give HCl salt, mp 50–53° C. Yield was 39%.

MS m/z(EI direct): 452(M⁺), 437, 395, 341, 285, 236, 98.

Anal. Calcd for $C_{28}H_{44}N_4O \cdot 2HCl \cdot 3.5H_2O$: C, 57.13; H, 9.07; N, 9.52. Found: C, 57.46; H, 9.19; N, 9.10.

A part of this hydrochloride salt was converted to free amine.

¹H NMR (270 MHz, CDCl₃) δ7.35–7.23 (2H, m), 7.05–6.80 (3H, m), 4.75 (2H, s), 3.53 (2H, t, J=6.5 Hz), 3.00–2.60 (4H, m), 2.54 (2H, t, J=6.5 Hz), 2.50–2.38 (4H, m), 2.00–1.22 (22H, m), 0.95 (3H, s).

Preparation 2

1-(4-Oxo-1-phenyl-1,3,8-triazaspiro[4.5]dec-8-yl)-4-cycloheptene-1-carbonitrile

This was prepared according to the procedure described in Preparation 1 using 4-cycloheptenone (J. A. Marshall et al. J. Org. Chem. 1982, 47, 693) instead of cycloheptanone. Yield was 65%.

¹H NMR (270 MHz, CDCl₃) δ7.40 (1H, br.s), 7.35–7.23 (2H, m), 7.00–6.83 (3H, m), 5.85–5.70 (2H, m), 4.76 (2H, s), 3.10–2.95 (4H, m), 2.70–2.30 (4H, m), 2.25–2.00 (4H, m), 1.95–1.70 (4H, m).

Example 6

8-(1-Methyl-4-cyclohepten-1-yl)-1-phenyl-1,3,8-triazaspiro[4.5]decan-4-one

This was prepared according to the procedure described in Example 4 using 1-(4-oxo-1-phenyl-1,3,8-triazaspiro[4.5]dec-8-yl)-4-cycloheptene-1-carbonitrile instead of 1-(4-oxo-1-phenyl-1,3,8-triazaspiro[4.5]dec-8-yl)cycloheptanecarbonitrile. Yield was 16%.

¹H NMR (270 MHz, CDCl₃) δ7.36–7.23 (3H, m), 6.98–6.78 (3H, m), 5.83–5.70 (2H, m), 4.75 (2H, s), 3.02–2.60 (6H, m), 2.50–2.35 (2H, m), 2.05–1.65 (6H, m), 1.50–1.35 (2H, m), 0.95 (3H, s).

This free amine was converted to hydrochloride salt, mp 251–254° C.

IR(KBr):3400, 1713 cm⁻¹

MS(ESI positive) m/z: 340(M+H)⁺.

Anal. Calcd for $C_{21}H_{29}N_3O \cdot 2HCl \cdot 0.5H_2O$: C, 59.85; H, 7.65; N, 9.97. Found: C, 59.91; H, 7.99; N, 9.63.

Preparation 3

1-(4-Oxo-1-phenyl-1,3,8-triazaspiro[4.5]dec-8-yl)cyclohexane-carbonitrile

This was prepared according to the procedure described in Preparation 1 using 4-cyclohexanone instead of cycloheptanone. Yield was 81%.

¹H NMR (270 MHz, CDCl₃) δ7.40 (1H, br.s), 7.34–7.25 (2H, m), 7.02–6.85 (4H, m), 4.75 (2H, s), 3.06–2.98 (4H, m), 2.64–2.50 (2H, m), 2.22–2.06 (2H, m), 1.90–1.50 (10H, m).

Example 7

8-(1-Benzylcycloheptyl)-1-Phenyl-1,3,8-triazaspiro[4.5]decan-4-one

This was prepared according to the procedure described in Example 1 using 1-(4-oxo-1-phenyl-1,3,8-triazaspiro[4.5]dec-8-yl)cyclohexanecarbonitrile instead of 1-(4-oxo-1-phenyl-1,3,8-triazaspiro[4.5]dec-8-yl)cycloheptanecarbonitrile and benzylmagnesium bromide instead of phenylmagnesium bromide. Yield was 54%.

¹H NMR (270 MHz, CDCl₃) δ7.39–7.10 (7H, m), 7.00–6.94 (2H, m), 6.87–6.79 (1H, m), 6.42 (1H, br.s), 4.76 (2H, s), 3.10–2.90 (4H, m), 2.80–2.69 (2H, m), 2.68 (2H, s), 1.92–1.00 (12H, m).

This free amine was converted to hydrochloride salt, mp 237–241° C.

IR(KBr): 1709 cm⁻¹

Anal. Calcd for $C_{26}H_{33}N_3O \cdot HCl \cdot H_2O$: C, 68.18; H, 7.92; N, 9.17. Found: C, 68.06; H, 7.60; N, 8.87.

Example 8

3-(3-Aminopropyl)-8-(1-methylcycloheptyl)-1-phenyl-1,3,8-triazaspiro[4.5]decan-4-one This was prepared according to the procedure described in Example 2 using 8-(1-methylcycloheptyl)-1-phenyl-1,3,8-triazaspiro[4.5]decan-4-one instead of 1-phenyl-8-(1-phenylcycloheptyl)-1,3,8-triazaspiro[4.5]decan-4-one. Yield was 57%. Then Boc group was removed by treatment of HCl solution in methanol to give title compound as HCl salt, mp 216–220° C.

¹H NMR (270 MHz, DMSOd₆) δ10.35–10.20 (1H, m), 7.93 (3H, br.s), 7.20–7.05 (4H, m), 6.75–6.65 (1H, m), 4.63 (2H, s), 3.70–3.50 (4H, m), 3.10–2.90 (4H, m), 2.75–2.60 (4H, m), 2.10–1.40 (14H, m), 1.35 (3H, s).

IR(KBr): 3400, 1695 cm⁻¹

MS(ESI positive) m/z: 399(M+H)⁺.

Anal. Calcd for $C_{24}H_{38}N_4O \cdot 2HCl \cdot 0.5CH_2Cl_2$: C, 57.25; H, 8.04; N, 10.90. Found: C, 57.39; H, 7.89; N, 11.01.

Example 9

3-(6-Aminohexyl)-8-(1-phenylcycloheptyl)-1-phenyl-1,3,8-triazaspirol[4.5]decan-4-one This was prepared according to the procedure described in Example 2 using 8-(1-phenylcycloheptyl)-1-phenyl-1,3,8-triazaspiro[4.5]decan-4-one and 6-t- buthoxycarbonylaminohexyl mesylate instead of 3-buthoxycarbonylaminopropyl bromide. Yield was 73%. Then Boc group was removed by treatment with HCl solution in methanol to give the title compound as HCl salt.

$^1$H NMR (270 MHz, DMSOd$_6$) δ10.45 (1H, br.s), 7.94 (3H, br.s), 7.86–7.78 (2H, m), 7.53–7.43 (3H, m), 7.22–7.17 (4H, m), 6.81–6.73 (1H, m), 4.64 (2H, s), 3.70–3.50 (2H, m), 3.45–3.20 (2H, m), 3.20–3.00 (2H, m), 2.90–2.65 (4H, m), 2.50–2.45 (2H, m), 1.80–1.05 (20H, m).

IR(KBr): 3422, 1688 cm$^{-1}$

Anal. Calcd for $C_{32}H_{46}N_4O.2HCl.0.5H_2O$: C, 65.74; H, 8.45; N, 9.58. Found: C, 65.34; H, 8.15; N, 9.44.

Example 10

3-(6-Aminohexyl)-8-(1-methylcycloheptyl)-1-phenyl-1,3,8-triazaspiro[4.5]decan-4-one This was prepared according to the procedure described in Example 2 using 8-(1-methylcycloheptyl)-1-phenyl-1,3,8-triazaspiro[4.5]decan-4-one instead of 1-phenyl-8-(1-phenylcycloheptyl)-1,3,8-triazaspiro[4,5]decan-4-one and 6-t-buthoxycarbonylaminohexyl mesylate instead of 3-t-buthoxycarbonylaminopropyl bromide. Yield was 35%. Then Boc group was removed by treatment with HCl solution in methanol to give title compound as HCl salt.

$^1$H NMR (270 MHz, DMSOd$_6$) δ10.50 (1H, br.s), 7.97 (3H, br.s), 7.23–7.13 (4H, m), 6.82–6.74 (1H, m), 4.70 (2H, s), 3.78–3.60 (2H, m), 3.55–3.44 (2H, m), 3.20–3.04 (2H, m), 2.78–2.68 (2H, m), 2.20–2.05 (2H, m), 1.90–1.25 (25H, m).

IR(KBr): 3398, 1686 cm$^{-1}$

Anal. Calcd for $C_{27}H_{44}N_4O.2HCl.1.5H_2O$: C, 59.99; H, 9.14; N, 10.36. Found: C, 59.78; H, 9.33; N, 10.22.

Preparation 4

3-t-Buthoxycarbonylmethyl-1-phenyl-8-(1-phenylcycloheptyl)-1,3,8-triazaspiro[4.5]decan-4-one This was prepared according to the procedure described in Example 2 using 8-(1-phenylcycloheptyl)-1-phenyl-1,3,8-triazaspiro[4.5]decan-4-one and t-buthyl 2-bromoacetate instead of 3-buthoxycarbonylaminopropyl bromide. Yield was 100%.

$^1$H NMR (270 MHz, CDCl$_3$) δ7.60–7.50 (2H, m), 7.35–7.10 (5H, m), 7.00–6.80 (3H, m), 4.71 (2H, s), 4.01 (2H, s), 3.00–2.45 (6H, m), 2.20–2.00 (4H, m), 1.85–1.40 (10H, m), 1.46 (9H, s).

MS(EI) m/z: 517(M+), 489, 460, 404, 344, 289, 233, 91.

Example 11

3-[2-(4-Aminopiperidin-1-yl)ethyl]-8-(1-phenylcycloheptyl)-1-phenyl-1,3,8-triazaspiro[4.5]decan-4-one To a stirred suspension of LiAlH$_4$ (191 mg, 5.03 mmol) in THF (2 ml) was added a solution of 3-t-buthoxycarbonylmethyl-1-phenyl-8-(1-phenylcycloheptyl)-1,3,8-triazaspiro[4.5]decan-4-one (prepared in Preparation 4, 650 mg, 1.26 mmol) in THF (4 ml) at 0° C. After 1h stirring at room temperature, excess LiAlH$_4$ was quenched with Na$_2$SO$_4$-10H$_2$O (1.61 g) and KF (291 mg). After 1 h stirring at room temperature, the mixture was diluted with CH$_2$Cl$_2$ and the solid was removed by Celite filtration. The filtrate was concentrated and purified by preparative TLC (1 mm plate×4, n-hexane/acetone:3/1) to give 177 mg (31%) of alcohol derivative as white amorphous solid. To a solution of this alcohol derivative (177 mg, 0.396 mmol) and NEt$_3$ (82.8 μl, 0.594 mmol) in CH$_2$Cl$_2$ (2 ml) was added mesyl chloride (46 μl, 0.594 mmol) at 0° C. After 1 h stirring at room temperature, NaHCO$_3$ solution was added to the reaction mixture and extracted with CH$_2$Cl$_2$. The extracts combined were washed with brine, dried (Na$_2$SO$_4$), filtered, and concentrated to give 226 mg of pale yellow amorphous solid. A mixture of this mesylate derivative (226 mg, 0.396 mmol), 4-t-buthoxycarbonylaminopiperidine (166 mg, 0.99 mmol), K$_2$CO$_3$ (137 mg, 0.99 mmol), and DMF (5 ml) was stirred at 60° C. for 15 h and at 80° C. for 4 h. After cooling down to room temperature, the reaction mixture was diluted with water and extracted with mixed solvent (ethyl acetate/toluene). The extracts combined were washed with water and brine, dried (Na$_2$SO$_4$), filtered, and concentrated to give pale brown oil, which was purified by preparative TLC (1 mm plate×3, CH$_2$Cl$_2$/MeOH:15/1) to give 131 mg (53%) of Boc derivative as white amorphous solid. A solution of this Boc derivative (131 mg, 0.208 mmol) in HCl solution in methanol (10 ml) was stirred at room temperature for 20 h. After evaporation of the solvent, the residue was diluted with 25% NH$_4$OH and CH$_2$Cl$_2$. The organic layer was separated and washed with brine, dried (Na$_2$SO$_4$), filtered, and concentrated. The residue was purified by preparative TLC (0.5 mm plate×3, CH$_2$Cl$_2$/MeOH:10/1) to give 81.5 mg (74%) of colorless oil as title compound.

$^1$H NMR (270 MHz, CDCl$_3$) δ7.60–7.50 (2H, m), 7.35–7.15 (5H, m), 6.96–6.80 (3H, m), 4.69 (2H, s), 3.50 (2H, t, J=6.4 Hz), 3.00–2.45 (11H, m), 2.20–2.00 (6H, m), 1.85–1.20 (16H, m).

MS(EI) m/z: 529(M+), 356, 301, 251, 127, 91.

This was converted to fumaric acid salt to give 78 mg of pale yellow amorphous solid.

IR(KBr): 3400, 1693 cm$^{-1}$

Anal. Calcd for $C_{33}H_{47}N_5O.1.5C_4H_4O_4.1.5H_2O$: C, 64.09; H, 7.72; N, 9.58. Found: C, 64.34; H, 7.92; N, 9.29.

Example 12

3-Methoxycarbonylmethyl-1-phenyl-8-(1-phenylcycloheptyl)-1,3,8-triazaspiro[4.5]decan-4-one A mixture of 3-t-butoxycarbonylmethyl-1-phenyl-8-(1-phenylcycloheptyl)-1,3,8-triazaspiro[4.5]decan-4-one (prepared in Preparation 4, 100 mg, 0.193 mmol) and HCl solution in methanol (10 ml) was stirred at 60° C for 16 h. After evaporation of the solvent, the residue was basified with 25% NH$_4$OH and extracted with CH$_2$Cl$_2$. The extracts combined were dried(Na$_2$SO$_4$), filtered, and concentrated. The residue was purified by preparative TLC (1 mm plate×2, hex/acetone:5/2) to give 68.8 mg (75.1%)of title compound as white amorphous solid.

$^1$H NMR (270 MHz, CDCl$_3$)δ7.56–7.50 (2H, m), 7.34–7.14 (5H, m), 6.98–6.83 (3H, m), 4.72 (2H, s), 4.16 (2H, s), 3.75 (3H, s), 2.95–2.72 (4H, m), 2.58–2.42 (2H,m), 2.20–1.99 (4H, m), 1.85–1.40 (10H, m).

This was converted to HCl salt by treating with HCl solution in methanol.

IR(KBr):3391, 1747, 1699 cm$^{-1}$

Anal. Calcd for $C_{29}H_{37}N_3O_3.HCl$: C, 68.02; H, 7.48; N, 8.21. Found: C, 67.69; H, 7.51; N, 8.17.

The chemical structures of the compounds of Formula (I) prepared in the Examples 1 to 12, are summarized in the following table.

TABLE

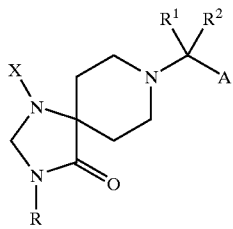

(I)

| Example No. | $R^1$ | $R^2$ | R | A | X |
|---|---|---|---|---|---|
| 1 | cycloheptyl | hydrogen | | phenyl | phenyl |
| 2 | cycloheptyl | aminopropyl | | phenyl | phenyl |
| 3 | cycloheptyl | piperidinylethyl | | phenyl | phenyl |
| 4 | cycloheptyl | hydrogen | | methyl | phenyl |
| 5 | cycloheptyl | piperidinylethyl | | methyl | phenyl |
| 6 | cycloheptenyl | hydrogen | | methyl | phenyl |
| 7 | cyclohexyl | hydrogen | | benzyl | phenyl |
| 8 | cycloheptyl | aminopropyl | | methyl | phenyl |
| 9 | cycloheptyl | aminohexy-6-yl | | phenyl | phenyl |
| 10 | cycloheptyl | aminohexy-6-yl | | methyl | phenyl |
| 11 | cycloheptyl | 2-(4-amino-piperidin-1-yl)ethyl | | phenyl | phenyl |
| 12 | cycloheptyl | methoxycarbonyl-methyl | | phenyl | phenyl |

What is claimed is:

1. A compound of the following formula:

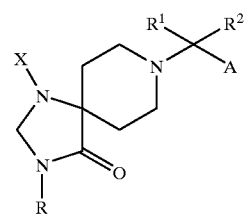

(I)

or its pharmaceutically acceptable salt, wherein $R^1$ and $R^2$, taken together with the carbon atom to which they are attached, form a mono-, bi-, or tri-cyclic group having 3 to 13 carbon atoms, wherein the cyclic group is optionally substituted by one to five substituents independently selected from halo, $(C_1-C_4)$alkyl, $(C2-C_4)$alkenyl, $(C_1-C_4)$alkoxy, hydroxy, oxo, $=CH_2$ and $=CH-(C_1-C_4)$alkyl, provided that the bi- or tri-cyclic group is not a benzo-fused ring;

A is $(C_2-C_5)$alkenyl, $(C_2-C_5)$alkynyl, phenyl-$(C_1-C_5)$ alkyl, phenyl or heteroaryl selected from furyl, thienyl, pyrrolyl and pyridyl, wherein the phenyl and heteroaryl are optionally substituted by one to three substituents selected from halo, $(C_1-C_3)$alkyl and $(C_1-C_3)$alkoxy;

R is hydrogen, $(C_1-C_6)$alkyl, $(C_2-C_6)$alkenyl, $(C_2-C^6)$ alkynyl, $(C_3-C_7)$cycloalkyl, $(C_1-C_6)$alkanoyl, $((C_1-C_4)$alkyl$)$-Z—$(C_1-C_6)$alkynyl, $((C_3-C_7)$ cycloalkyl$)$-Z—$(C_1-C_6)$alkyl, heterocyclic-$(C_1-C_6)$ alkyl, phenyl-$(C_1-C_6)$alkyl, heterocyclic-$(C_1-C_6)$ alkyl-Z—$(C_1-C_6)$alkyl, phenyl-$(C_1-C_6)$alkyl-Z— $(C_1-C_6)$alkyl, heterocyclic- Z—$(C_1-C_6)$alkyl, $((C_3-C_7)$cycloalkyl$)$-heterocyclic-$(C_1-C_6)$alkyl, heterocyclic-heterocyclic- Z—$(C_1-C_6)$alkyl, wherein the alkyl, alkenyl, alkynyl, cycloalkyl and heterocyclic are optionally substituted by one to three substituents selected from halo, hydroxy, amino, guanizino, carboxy, amidino, ureido, $(C_1-C_3)$alkyl, $(C_1-C_3)$ alkoxy, and mono- or di-$(C_1-C_4)$alkylamino, and wherein Z is O, S, SO, $SO_2$, CO, C(=O)O, OC(=O), N(R), C(=O)N(R) or N(R)CO; and X is phenyl, heterocyclic, $(C_1-C_6)$alkyl, $(C_2-C_6)$alkenyl, $(C_3-C_7)$cycloalkyl, $(C_2-C_7)$alkynyl, wherein the phenyl, heterocyclic, alkyl, alkenyl, cycloalkyl and alkynyl are optionally substituted by one to three substituents selected from halo, $(C_1-C_3)$alkyl and $(C_1-C_3)$alkoxy.

2. A compound according to claim 1, wherein $R^1$ and $R^2$, taken together with the carbon atom to which they are attached, form a monocyclic group selected from $(C_3-C_{13})$cycloalkyl and $(C_3-C_{13})$cycloalkenyl, wherein the monocyclic group is optionally substituted by one or two substituents independently selected from halo and $(C_1-C_4)$alkyl;

A is phenyl-$(C_1-C_5)$alkyl or phenyl optionally substituted by one to three substituents independently selected from halo, $(C_1-C_3)$alkyl and $(C_1-C_3)$alkoxy, R is hydrogen, $(C_1-C_6)$alkyl, $(C_2-C_6)$alkenyl, heterocyclic-$(C_1-C_6)$alkyl or $((C_1-C_4)$alkyl$)$-Z— $(C_1-C_6)$alkyl, wherein the alkyl, alkenyl and heterocyclic are optionally substituted by one to three substituents selected from halo, hydroxy, amino, guanizino, carboxy, amidino, ureido, $(C_1-C_3)$alkyl, $(C_1-C_3)$ alkoxy, mono- and di-$(C_1-C_4)$alkylamino; and X is phenyl, heterocyclic, $(C_1-C_6)$alkyl or $(C_2-C_6)$ alkenyl, wherein the phenyl, heterocyclic, alkyl and alkenyl are optionally substituted by one to three substituents selected from halo, $(C_1-C_3)$alkyl and $(C_1-C_3)$ alkoxy.

3. A compound according to claim 2, wherein $R^1$ and $R^2$, taken together with the carbon atom to which they are attached, form a monocyclic group selected from $(C_5-C_{10})$ cycloalkyl and $(C_5-C_{10})$cycloalkenyl, wherein the monocyclic group is optionally substituted by one or two substituents independently selected from $(C_1-C_3)$alkyl; A is phenyl or benzyl; R is hydrogen, $(C_1-C_3)$alkyl, amino-$(C_1-C_6)$ alkyl, heterocyclic-$(C_1-C_3)$alkyl wherein the heterocyclic is optionally substituted by amino or $((C_1-C_4)$alkyl$)$-Z— $(C_1-C_6)$alkyl wherein Z is OC(=O); and X is $(C_1-C_3)$alkyl or phenyl.

4. A compound according to claim 3, wherein $R^1$ and $R^2$, taken together with the carbon atom to which they are attached, form cyclohexyl, cycloheptyl or cycloheptenyl; A is phenyl or benzyl; R is hydrogen, aminopropyl, aminohexyl, piperidinylethyl, 4-aminopiperidinylethyl or methoxy-carbonylmethyl; and X is phenyl.

5. A compound selected from 3-(3-aminopropyl)-1-phenyl-8-(1-phenylcycloheptyl)-1,3, 8-triazaspirol[4.5]decan-4-one; and 8-(1-methylcycloheptyl)-1-phenyl-1,3,8-triazaspiro[4.5] decan-4-one; and its pharmaceutically acceptable salts.

6. A pharmaceutical composition for the treatment of a disorder or condition in a mammal, wherein the disorder or condition is selected from the group consisting of inflammatory diseases, inflammation-related hyperalgesia, and pain, comprising an amount of a compound of claim 1, or a pharmaceutically acceptable salt thereof that is effective in treating such disorder or conditions and a pharmaceutically acceptable carrier.

7. A method of treating a disorder or condition in a mammal, where the disorder or condition is selected from the group consisting of inflammatory diseases, inflammation-related hyperalgesia, and pain, comprising administering to said mammal an effective amount of the compound of claim 1, or a pharmaceutically acceptable salt thereof, and a pharmaceutically acceptable carrier.

* * * * *